(12) United States Patent
Higashi et al.

(10) Patent No.: US 7,791,729 B2
(45) Date of Patent: Sep. 7, 2010

(54) ATTENUATED TOTAL REFLECTION PROBE AND SPECTROMETER THEREWITH

(75) Inventors: Noboru Higashi, Osaka (JP); Yukihiro Ozaki, Hyogo (JP); Akifumi Ikehata, Hyogo (JP)

(73) Assignee: Kurashiki Boseki Kabushiki Kaisha, Okayama (JP)

( * ) Notice: Subject to any disclaimer, the term of this patent is extended or adjusted under 35 U.S.C. 154(b) by 223 days.

(21) Appl. No.: 12/073,532

(22) Filed: Mar. 6, 2008

(65) Prior Publication Data
US 2008/0218734 A1    Sep. 11, 2008

(30) Foreign Application Priority Data
Mar. 8, 2007    (JP) .......................... P2007-058895

(51) Int. Cl.
*G01N 21/55* (2006.01)
(52) U.S. Cl. .................................... 356/445
(58) Field of Classification Search ................. 356/303, 356/326, 445
See application file for complete search history.

(56) References Cited

U.S. PATENT DOCUMENTS

| | | | |
|---|---|---|---|
| 4,826,313 A | 5/1989 | Schar et al. | |
| 5,097,130 A | 3/1992 | Koashi et al. | |
| 6,929,943 B1 | 8/2005 | Quapil et al. | |

FOREIGN PATENT DOCUMENTS

| | | | |
|---|---|---|---|
| JP | 62-75230 A | 4/1987 | |
| JP | 3-175341 A | 7/1991 | |
| JP | 7-12716 A | 1/1995 | |
| JP | 2005-214863 A | 8/2005 | |
| JP | 2005-233884 A | 9/2005 | |
| JP | 2005233884 A | * 9/2005 | |
| WO | WO-2006/109408 A1 | 10/2006 | |

OTHER PUBLICATIONS

Higashi et al., "Potential of Far-Ultraviolet Absorption Spectroscopy as a Highly Sensitive Quantitative and Qualitative Analysis Method for Aqueous Solutions," Part I: Determination of Hydrogen Chloride in Aqueous Solutions, Applied Spectroscopy, 2004, pp. 910-916 vol. 58, No. 8.

Higashi et al., "An attenuated total reflectance far-UV spectrometer", Review of Scientific Instruments 2007, vol. 78, pp. 103107-103107-5.

* cited by examiner

*Primary Examiner*—Roy Punnoose
(74) *Attorney, Agent, or Firm*—Birch Stewart Kolasch & Birch, LLP

(57) ABSTRACT

An attenuated total reflection probe has a prism and a supporter. The prism is made of an optical material which transmits light in far ultraviolet region, and has a contact plane to be in contact with a sample, and an incoming plane and an outgoing plane both not to be in contact with the sample. The supporter has an opening and is connected hermetically with the prism around the opening and eventually exposes the contact plane facing the opening. The contact plane, the incoming plane and the outgoing plane of the prism are formed such that light transmitting the incoming plane enters the contact plane at an incident angle larger than critical angle and that the light totally reflected by the contact plane goes out through the outgoing plane.

7 Claims, 4 Drawing Sheets

EVANESCENT WAVE
PENETRATION DEPTH

ATTENUATED TOTAL REFLECTION PROBE AND SPECTROMETER THEREWITH

BACKGROUND OF THE INVENTION

1. Technical Field

The invention relates to spectral analysis in far ultraviolet region.

2. Background Art

Recently, it is needed more and more to measure a very small change in the purity or characteristics of water in an aqueous solution, without changing the quality of water. For example, in a process for fabricating a semiconductor device, an aqueous solution is required to have high purity in correspondence to electrical resistivity of water at a level near theoretical limit. Specially purified water expected to have a particular effect by dissolving subtle gas such as ozone or hydrogen is also used recently.

In qualitative and quantitative analysis of water or soluble components therein, spectral analysis is used in various ways as a very powerful tool. Spectral analysis technique is divided mainly into ultraviolet and visible spectroscopy, near infrared spectroscopy and infrared spectroscopy with reference to wavelength region to be measured.

Especially, in near infrared spectroscopy, absorption spectra due to hydrogen bonds that are characteristic of water are observed noticeably in 800-1,400 nm region. For example, Japanese Patent laid open Publication H03-175341/1991 proposes to measure solute components with spectroscopy. Hydrogen bonds are formed between water molecules in water, and the state of hydrogen bond is changed very sensitively due to dissolved solutes into water. By studying a change in spectra, the dissolved components can be analyzed quantitatively. In concrete, when inorganic electrolytes are dissociated as ions in an aqueous solution, bonding state of water molecules themselves or a hydrogen bond between a water molecule near a hydrated ion and a water molecule in bulk water is affected due to disconnection or distortion of the hydrogen bonds. Then, near infrared spectra of an aqueous solution becomes different from that of pure water. By using a predetermined calibration curve, a concentration of an ion species can be measured quantitatively not from the absorption spectra of the ion species, but from that of water.

It is proposed recently to measure far ultraviolet spectra in order to determine a concentration of hydrated substance in an aqueous solution (Japanese Patent laid open Publication 2005-214863, and Applied Spectroscopy Vol. 58, No. 8 (2004) 910-916). This is based on a fact that far ultraviolet spectra of water are closely related to the state of hydrogen bond in water, similarly to the above-mentioned near infrared spectra. The absorption spectra of water has a peak around 150 nm of wavelength due to n→σ* transition, and the peak is shifted towards longer wavelengths due to an effect of electric field generated by water molecule itself and a hydrated ion. Therefore, a part of the absorption spectra is shifted into a wavelength region that can be measured with a conventional spectroscopy apparatus (a spectroscopy apparatus that does not need a vacuum system or nitrogen gas purge). By measuring the far ultraviolet spectra, an aqueous solution can be analyzed qualitatively, and solutes of very small concentrations can be measured quantitatively. This analysis using the far ultraviolet spectra of water is much sensitive qualitatively and quantitatively than that using the near infrared spectra. However, because the absorbance of water itself is very large in far ultraviolet region, the spectra can be measured only in a wavelength region longer than 180 nm which corresponds to a lower limit of transmission spectra.

Attenuated total reflection (ATR) spectrometry is explained here because it is used in the invention for measuring absorption spectra of a material having very large absorption. By using attenuated total reflection spectrometry, absorption in a sample can be measured due to penetration of light into the sample (evanescent wave) in the order of wavelength extending from a surface of an optical probe at which the light is reflected totally. The absorption spectra obtained is analogous theoretically to that measured with cell length of the order of wavelength. It is proposed in Japanese Patent laid open Publication S62-75230/1987 to measure a thick solution with an ATR probe. Synthetic quartz or sapphire is used as a material for fabricating the optical probe. In, for example, Japanese Patent laid open Publication H07-12716/1995, it is proposed to enhance the sensitivity of attenuated total reflection spectrometry itself.

The absorption observed in the absorption spectra of water in near infrared region is weak because it is ascribed to an inherently forbidden transition, so that very small concentration of a solute in an aqueous solution cannot be measured. Then, there is a need to measure a very small concentration of solute that cannot be measured with a significant difference in near infrared region. On the other hand, water has a large absorption peak around 150 nm of wavelength. By detecting a change in absorption spectra in far ultraviolet region, solutes in an aqueous solution can be measured qualitatively and quantitatively with a much higher sensitivity than in near infrared spectra. However, the absorption of far ultraviolet light of water is a large obstacle for spectral measurement of water or an aqueous solution in far ultraviolet region. If a substance other than water has strong absorption in far ultraviolet region, the absorption thereof is also a large obstacle for spectral measurement. It is to be noted that the prior art attenuated total reflection techniques mentioned above applied to infrared and visible regions cannot be applied to far ultraviolet region because transmittance is not sufficiently large in far ultraviolet region or the optical probe cannot cause total reflection at a surface in contact with a sample substance.

SUMMARY OF THE INVENTION

An object of the invention is to measure spectra easily in far ultraviolet region equal to or shorter than 180 nm of wavelength.

An attenuated total reflection probe of an embodiment has a prism and a supporter. The prism, made of an optical material which transmits light in far ultraviolet region, has a contact plane to be in contact with a sample, and an incoming plane and an outgoing plane both not to be in contact with the sample. The supporter has an opening and is connected hermetically with the prism around the opening. Thus, the supporter eventually exposes the contact plane facing the opening to the sample. The contact plane, the incoming plane and the outgoing plane of the prism are formed such that light transmitting the incoming plane enters the contact plane at an incident angle larger than critical angle and that the light totally reflected by the contact plane goes out through the outgoing plane.

A spectrometer of an embodiment has the attenuated total reflection probe. A light source radiates ultraviolet light towards the attenuated total reflection probe, and a photodetector detects light received from the attenuated total reflection probe. An optical element for dispersing ultraviolet light is provided in an optical path from the light source to the photodetector.

An advantage of the invention is that spectroscopy is performed in far ultraviolet region for a substance having large absorbance.

BRIEF DESCRIPTION OF THE DRAWINGS

These and other objects and features of the present will become clear from the following description taken in conjunction with the preferred embodiments thereof with reference to the accompanying drawings, and in which.

DETAILED DESCRIPTION OF THE PREFERRED EMBODIMENTS

Figure 1:
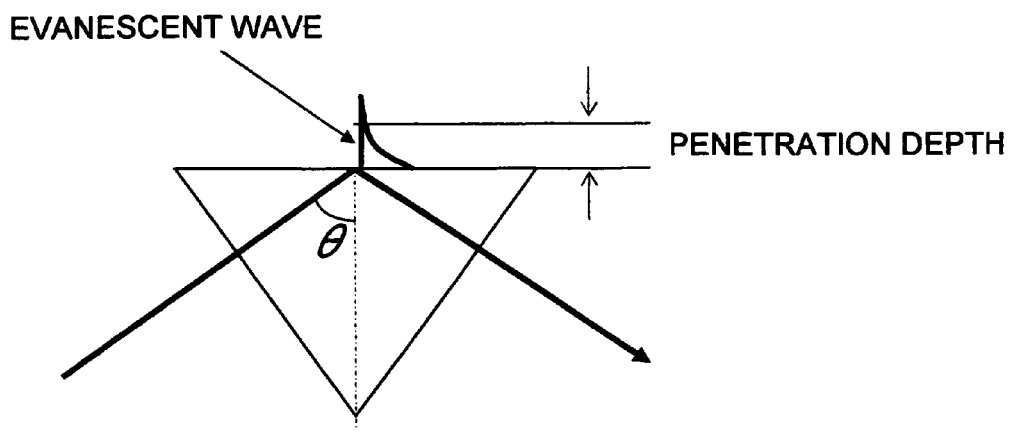
FIG. 1 is a schematic diagram of a structure of a general attenuated total reflection probe.

Embodiments of the invention will be explained below by referring to the drawings, wherein like reference characters designate like or corresponding parts throughout the several views.

Figure 2:
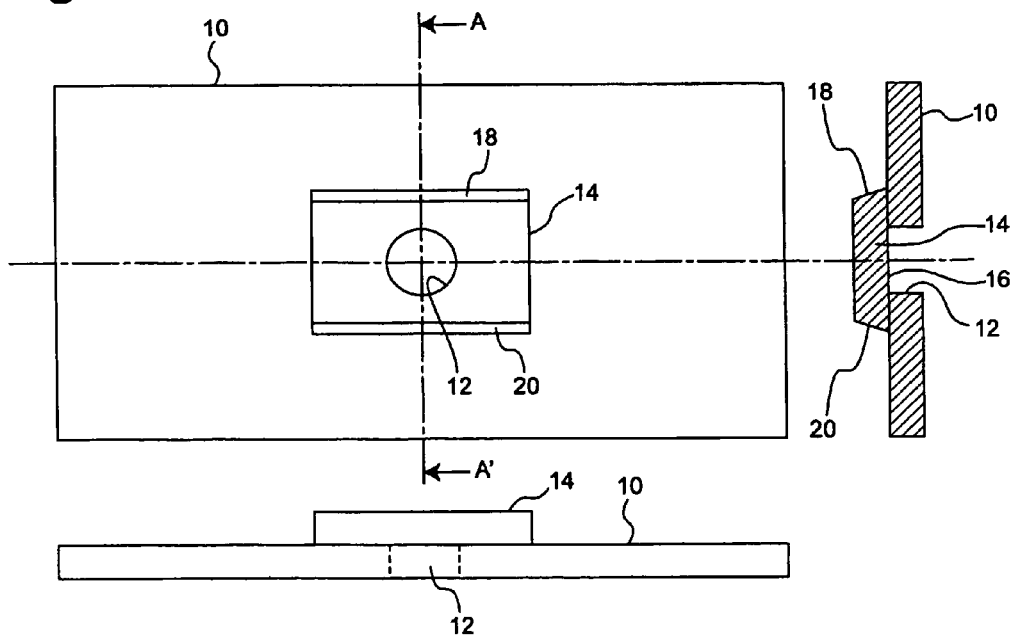
FIG. 2 is a plan view, a front view and a side view of an optical probe.

Because absorption spectra of water in near infrared region have weak absorption ascribed inherently to the forbidden transition, a very small concentration of a solute cannot be measured with near infrared spectroscopy. Then the inventors studied far ultraviolet spectra and found that pure water has a very high absorption peak around 150 nm of wavelength in far ultraviolet region and that a very small concentration of a solute hydrated in an aqueous solution can be determined by measuring a change in far ultraviolet spectra at a slope of the high absorption peak. In other words, the spectra decrease sharply in far ultraviolet region from the absorption peak around 150 nm to absorption bottom around 200 nm, and the peak position and the band width of the absorption band are affected even by hydration of a very small amount of solute. Therefore, a very small wavelength shift of the absorption peak can be detected with very high sensitivity in the slope of the absorption peak, and this can be used to measure a very small concentration of a solute in an aqueous solution. This is disclosed in Japanese Patent laid open Publication 2005-214863. A very small amount of a solute can be measured with a calibration curve determined with multivariate analysis of absorbance measured at a plurality of wavelengths in the slope of the absorption peak of water. For example, in Japanese Patent laid open Publication 2005-214863 FIG. 1 shows far ultraviolet spectra of hydrogen chloride (HCl) solutions of eleven concentrations between 0 and 20 parts per million (ppm) (or 1, 2, 3, 4, 5, 6, 8, 10, 12, 16 and 20 ppm), and FIG. 2 shows correlation of a calibration model for predicting a concentration of HCl. The correlation coefficient R is 0.9987, and the standard deviation is 0.18 ppm. It is found that a very small amount of HCl can be measured at high precision at least up to 100 ppm. The detection limit of HCl in an aqueous solution is 0.5 ppm in the example of measurement.

In the above-mentioned example of measurement on water and aqueous solution, wavelengths to be measured are limited to 190 to 210 nm in the slope of the absorption band of water. This is ascribed to difficulty in measuring transmission spectra in a wavelength region shorter than 180 nm. For example, because the absorbance in the absorption band having a peak at around 150 nm is very large, the cell length along which light transmits a sample in a cell has to be decreased to the order of a few hundred nm. It is also necessary to remove oxygen that absorbs ultraviolet light in a measurement environment. On the other hand, in order to analyze solutes in an aqueous solution with higher sensitivity, it is needed to measure a slope of the absorption peak in a wavelength region between 160 to 180 nm wherein a change in absorption spectra appears larger though the absorption is large.

In order to measure spectra of water or aqueous solution around the absorption peak (150 nm) in far ultraviolet region, the cell length has to be as short as about 100 nm. Then, the inventors take notice of attenuated total reflection (ATR) known as a spectrometry for absorption spectra of a material having very large absorbance. In the method disclosed in Japanese Patent laid open Publication 2005-214863 for measuring solute concentrations in an aqueous solution with far ultraviolet spectra, the solute concentration is measured not based on spectra of water, but based on the absorption bands of the solutes. On the other hand, by using an optical probe for attenuated total reflection spectrometry (hereinafter referred to also as ATR probe) and a spectrometer therewith explained below, the above-mentioned analysis of Japanese Patent laid open Publication 2005-214863 can be extended to the wavelength region of 180 to 160 nm for a more sensitive measurement.

Attenuated total reflection spectrometry is explained here. FIG. 1 shows an interface between an upper side of a prism made of a material having a higher index of refraction such synthetic quartz (synthetic silica) and a material having a lower index of refraction such as a sample to be measured, for example, water. When light is incident on the interface from a side of the prism, it is reflected totally if the incident angle θ is larger than critical angle. Though the light is reflected totally on total reflection, the light also penetrates into the material of lower index of refraction by the order of wavelength. It propagates along the interface and is reflected thereafter. The light penetrating into the material of lower index of refraction is called evanescent wave. The electric field of the evanescent wave is highest at the reflection point and attenuates sharply along the interface and in the direction perpendicular to the interface. In FIG. 1, the change in electric field of the evanescent wave is shown schematically in the direction perpendicular to the interface. A distance at which the electric field of the evanescent wave attenuates by a ratio of 1/e is called penetration depth. By using attenuated total reflection, absorption of the evanescent wave (penetration of light of the order of wavelength on total reflection) can be measured as the absorption spectra. Because the penetration depth of light corresponds to optical path length in a conventional transmission spectra measurement, absorption spectra similar to transmission spectra with cell length of the order of wavelength can be obtained theoretically. Thus, a condition has to be satisfied that cell length of the order equal to or smaller than a few hundred nm in order to measure absorption spectra of water, and a requirement has to be satisfied that a measurement in the wavelength region between 160 and 180 nm is important for analysis on a very small amount of a solute in an aqueous solution. Then, it is proposed here to measure reflection/absorption spectra with an ATR probe in the wavelength region between 160 to 180 nm.

An optical probe used for attenuated total reflection measurements (ATR probe) should satisfy two following conditions in a wavelength region to be measured.

(A) Total reflection condition: The index of refraction of a material of the optical probe is larger than that of a sample.

(B) Transmission condition: The material of the optical probe is transparent.

Unfortunately, the index of refraction of water increases remarkably with decrease in wavelength in far ultraviolet region (refer to FIG. 4), and no material available now satisfies the two conditions for an ATR probe. For example, a material such as quartz or sapphire having index of refraction higher than water does not have sufficient transmittance around 160 nm, while a material such as magnesium fluoride or calcium fluoride that transmits far ultraviolet light in the wavelength region has index of refraction lower than water or does not satisfy the total reflection condition. Therefore, a prior art optical probe is available only for a wavelength region longer than 200 nm or at most 190 nm. In other words, an optical probe that can be used down to the peak wavelength around 150 nm is not yet reported.

The inventors propose an ATR probe of a single layer structure. However, before explaining the single-layer probe, a multi-layer ATR probe is commented here. The inventors study a multi-layer ATR probe on the above-mentioned two conditions on total reflection and transmission. In a multi-layer ATR, light propagates from a first optical material satisfying the transmission condition to a second optical material satisfying the total reflection condition. Then it is reflected by an interface between the second optical material and a sample. As to the measurement of attenuated total reflection of light, a second optical material such as quartz or sapphire having index of refraction higher than water in far ultraviolet region does not have sufficient transmittance around 160 nm, but if the optical path length in the optical material is shortened, transmission light remains, and the reflection/transmission spectra can be measured. For example, internal transmittance (transmittance of the material itself without considering reflection loss) in far ultraviolet region of synthetic quartz or sapphire having high transmittance in far ultraviolet region is equal to or higher than 50% around 160 nm for 1 mm of length. In a vertical-type three-layer structure, a second or central portion made of a material having higher index of refraction and lower transmittance and first portions at both sides of the second portion made of a material having lower index of refraction and higher transmittance. It is found that the optical length in the second portion can be decreased to have a value equal to or smaller than 1 mm. If the material of the second portion is quartz or sapphire of higher transmittance in far ultraviolet region, the optical length is as sufficiently short as or shorter than 5 mm even if it is longer than 1 mm, the internal transmittance remains 10% or more around 160 nm. Thus a multi-layer ATR probe is used for an ATR probe. Though it is found that such a multi-layer ATR probe can be realized, the inventors propose a different type of ATR probe or a single layer structure, as explained below.

Figure 3:
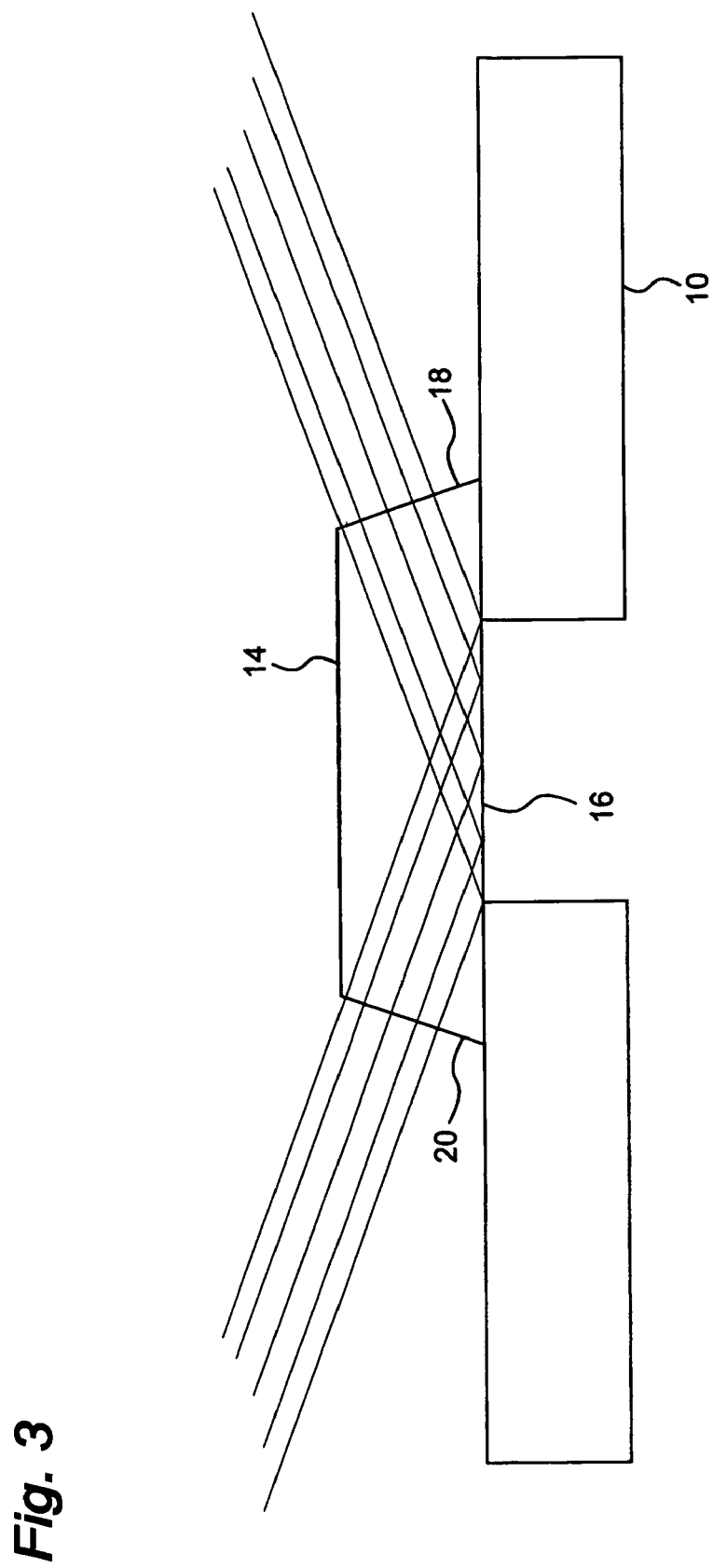
FIG. 3 is a diagram of a path of light entering into an optical probe.

FIGS. 2 and 3 show an optical probe according to an embodiment based on this concept. The optical probe has a rectangular supporting plate 10 having an opening 12 for access to a sample substance and a rectangular plate 14 made of a material with higher index of refraction. The supporting plate 10 is adhered with the rectangular plate 14 while sealing the opening 12 hermetically. The shape of the opening 12 is not limited to a circle, but may be, for example, a rectangle. The higher-index-of-refraction plate 14 covers the entire opening 12 of the supporting plate 10. A contact area between the higher-index-of-refraction plate 14 and the supporting plate 10 is adhered with optical contact or thermal melting. An adhesive is not favorable because impurities may be liable to migrate into a sample such as water or to form a void filled with sample within an adhesive layer. The supporting plate 10 is arranged to support the higher-index-of-refraction plate 14 on a side thereof to be in contact with sample substance such as water. The higher-index-of-refraction plate 14 contacts with the sample substance on a flat contact plane 16 in the opening 12. The higher-index-of-refraction plate 14 has an incoming plane 18 and an outgoing plane 20 opposing to each other, besides the contact plane 16. The two planes 18 and 20 do not contact with sample substance. The two planes 18 and 20 are flat, and an angle thereof relative to the contact plane 16 is set larger than critical angle for total reflection. The height or thickness of the higher-index-of-refraction plate 14 is determined based on the incident angle and the position and size of the opening 12 or the contact plane 16. In FIG. 3, parallel lines denote incoming and outgoing light. As shown in FIG. 3, ultraviolet light entering vertically the incoming plane 18 is subjected to total reflection at the contact plane 16 and enters vertically and transmits the outgoing plane 20. The higher-index-of-refraction plate 14 may have any shape except the above-mentioned geometrical condition on the incoming plane 18, the outgoing plane 20 and the contact plane 16, or it may not necessarily be a plate. Therefore, it may generally be called a prism as a transparent optical element with flat surfaces. The supporting plate 10 may not necessarily be a plate, and it may generally be called a supporter to provide the opening and the hermetic seal with the prism.

Figure 4:
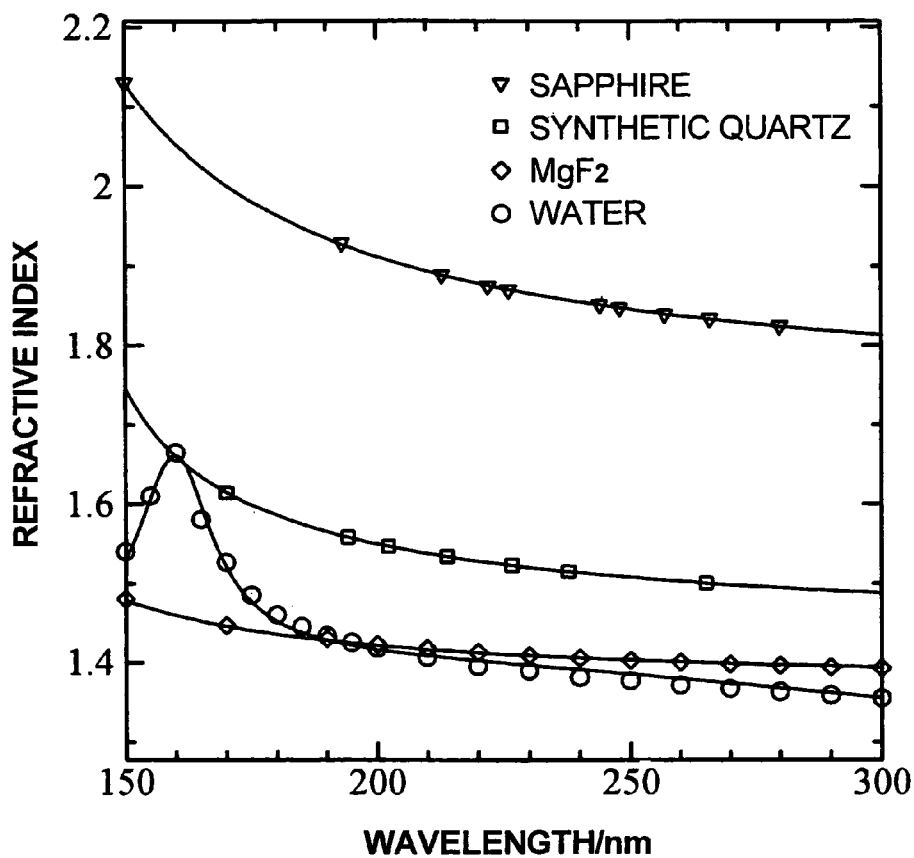
FIG. 4 is a graph of wavelength dependence of index of refraction of various optical materials in far ultraviolet region.

An optical material of the higher-index-of-refraction plate 14 has index of refraction higher than that of sample such as water in far ultraviolet region down to about 160 nm (total reflection condition). The optical material is, for example, synthetic quartz (SiO$_2$), quartz or sapphire. (FIG. 4 shows wavelength dependence of index of refraction of various materials such as sapphire, synthetic quartz (SiO$_2$) or quartz, water and magnesium fluoride, wherein solid lines represent approximation functions.) On the other hand, in the optical probe, the supporting plate 10 does not transmit light because it is arranged at the side of sample relative to the higher-index-of-refraction plate 14. Therefore, it is not needed that the supporting plate 10 has transmission characteristic in far ultraviolet region. Only good adhesion with the higher-index-of-refraction plate 14 is needed. The most desirable material for the supporting plate 10 is the same as that of the higher-index-of-refraction plate 14, but not limited thereto.

In an example, both the thickness of the supporting plate 10 and that of the higher-index-of-refraction plate 14 are 1 mm. The opening 12 of the supporting plate 10 has 2.0 mm of diameter. The higher-index-of-refraction plate 14 has a size of 5.0 mm by 4.0 mm. The angle between the incoming plane 18 or the outgoing plane 20 (or a side-plane of the higher-index-of-refraction plate 14) and the contact plane 16 is 110 degrees. In this example, the optical path through the optical material of the higher-index-of-refraction plate 14 is about 3.8 mm.

In the above-mentioned optical probe, if the optical material of the higher-index-of-refraction plate 14 to be in contact with sample substance is synthetic quartz having high transmittance in far ultraviolet region, the transmittance of far ultraviolet light of 160 nm of wavelength becomes about 70% at the interface with sample, and becomes about 50% after transmitting the higher-index-of-refraction plate 14. If the higher-index-of-refraction plate 14 is made of sapphire, the transmittance is about 20% after ultraviolet light of 150 nm goes out from the sapphire. In the above-mentioned probe, if the optical path length in the optical material is as sufficiently short as 5 mm or less, the internal transmittance is about 10% or more around 160 nm. Then the probe can be used as an ATR probe.

Generally, in the higher-index-of-refraction plate 14 satisfying the total reflection condition, the optical path length from the incoming plane 18 through the contact plane 16 to the outgoing plane 20 is set to have transmittance for 160 nm of wavelength equal to or larger than 10%, preferably equal to or larger than 20%, and more preferably equal to or larger than 50%. It is to be noted that reflectance at the interface with water around 160 nm is about 10%, depending on the index of refraction of the plate 14 and the incident angle of incoming light. A general spectrometer does not have sufficient resolution of measurement by considering stability of the apparatus when the remaining light intensity becomes smaller than one hundredth of that of the incoming light. Thus, the internal transmittance of light transmitting the optical material is required equal to or larger than 10%, as mentioned above.

Figure 5:
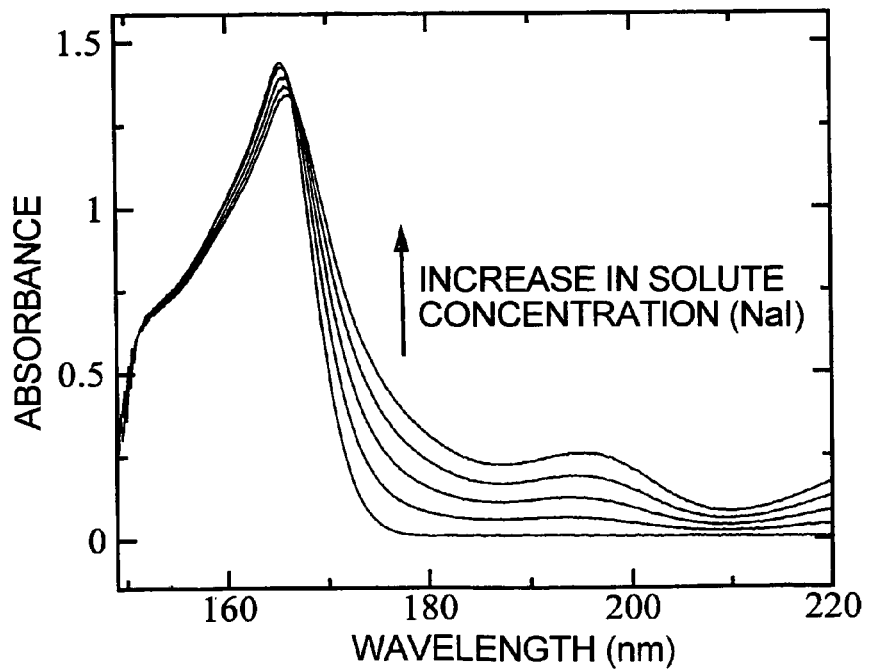
FIG. 5 is a graph of experimental data of absorbance plotted against solute concentration, measured with an optical probe made of sapphire.

An example of measurement data obtained with an ATR probe is explained below. FIG. 5 shows wavelength dependence of absorbance of aqueous solutions of different concentrations of solute (sodium iodide NaI) measured with an optical probe having the higher-index-of-refraction plate 14 made of sapphire. The incident angle is 60°. An absorption peak due to NaI is observed at around 195 nm. With increase in solute concentration, the absorption peak due to NaI rises, while the absorption peak of water shifts to longer wavelengths in the wavelength region below 180 nm. Quantitative analysis of the shift makes it possible to analyze the solute concentration more sensitively than that of the absorption peak due to NaI.

Figure 6:
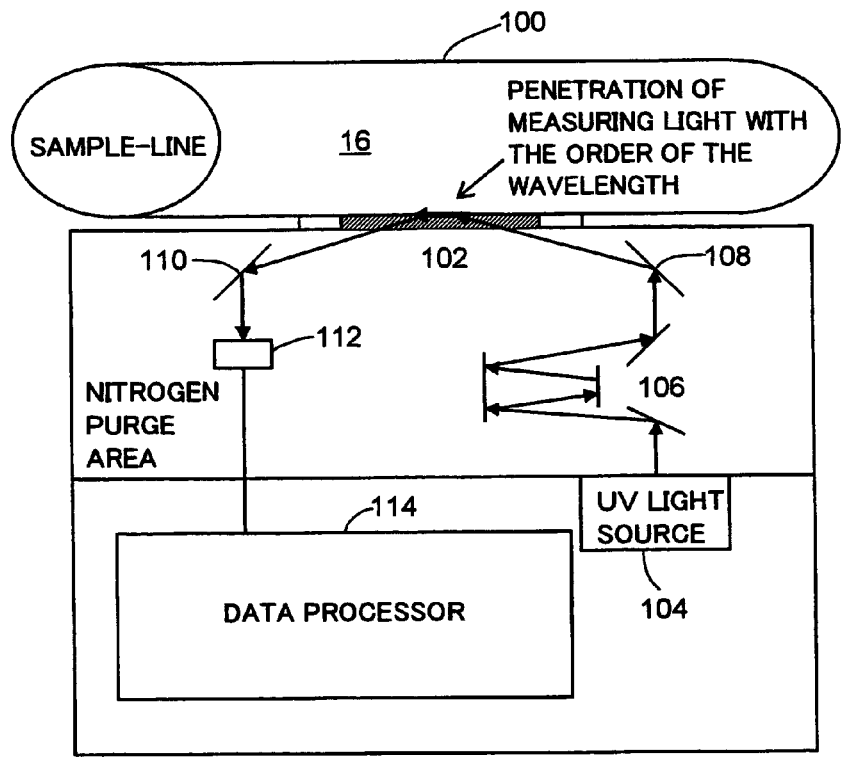
FIG. 6 is a block diagram of an apparatus for measuring a very small quantity of solute with far ultraviolet spectroscopy.

FIG. 6 shows a far ultraviolet spectrometer for measurement in a wavelength region between 160 and 210 nm with use of the above-mentioned optical probe or ATR probe. The spectrometer can be used to measure a very small solute concentration in an aqueous solution. An ATR probe 102 is provided to contact with sample substance 18 in a sample path 100. Alternatively, sample substance is introduced into a cell, and the optical probe is set to face with the sample substance in the cell. Alternatively, without using a cell, a wall of a pipe through which sample substance is introduced is used as a probe. An ultraviolet light source 104 such as a deuteron lamp radiates light, and the light passes a grating mirror 106 as a monochromator, is reflected by a mirror 108 and enters the optical probe 102. An optical element other than the grating mirror 106 may be used for dispersing ultraviolet light in an optical path from the light source to a photodetector. The incident angle of the light to the optical probe 102 is set appropriately. Light reflected from the optical probe 101 is reflected by a mirror 110 and enters the ultraviolet sensor 112. In the optical system explained above, nitrogen gas is introduced to purge oxygen gas from the optical system in the spectrometer. Alternatively, argon gas may be used to purge oxygen. Thus, oxygen gas in the optical path may be replaced with gas that does not absorb ultraviolet light. Alternatively, the optical system may be evacuated to vacuum. Spectra detected with the ultraviolet sensor 112 are processed by a data processor 114 wherein the absorbance is calculated from the measured data. A calibration curve is determined with a known multivariate analysis for absorbance at a plurality of wavelengths. In order to measure water spectra at 160 nm, cell length of about 100 nm is needed in a prior art spectrometer. In this embodiment a very short cell length is realized substantially by using the ATR probe, and the absorption peak of water can be measured. Further, the measurement can be performed real time. Because ultraviolet light penetrates into the sample by only a very short distance, the entire sample is not exposed substantially to ultraviolet light.

Figure 7:
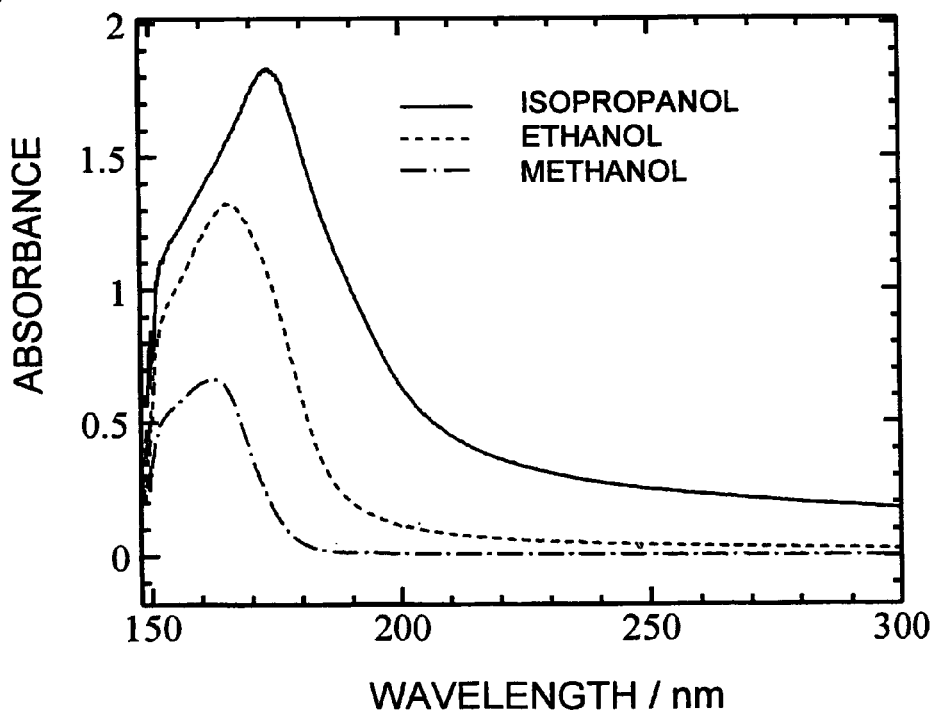
FIG. 7 is a graph of far ultraviolet spectra of substances other than water.

As will be understood by a person skilled in the art, the above-mentioned optical probe can be used to measure a liquid, gas or solid sample having large absorption in far ultraviolet region, besides water. For example, liquid such as isopropyl alcohol or gas such as oxygen can be measured. FIG. 7 shows examples of spectra of methanol, ethanol and isopropyl alcohol in far ultraviolet region measured with the higher-index-of-refraction plate 14 made of sapphire.

As explained above, spectroscopy in far ultraviolet region can be performed for a substance having large absorbance. Thus, very small amounts of solutes in an aqueous solution or the like can be detected easily with high sensitivity or can be measured quantitatively.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An attenuated total reflection probe comprising:
   a prism, made of an optical material which has index of refraction higher than water in far ultraviolet region, comprising a contact plane to be in contact with a sample, and an incoming plane and an outgoing plane both not to be in contact with the sample; and
   a supporter having an opening, connected with optical contact with the prism around the opening, the supporter eventually exposing the contact plane facing the opening;
   wherein the contact plane, the incoming plane and the outgoing plane of the prism are formed such that light transmitting the incoming plane enters the contact plane at an incident angle larger than critical angle and that the light totally reflected by the contact plane goes out through the outgoing plane.

2. The attenuated total reflection probe according to claim 1, wherein an optical path length from the incoming plane through the contact plane to the outgoing plane has internal transmittance equal to or larger than 10% for light of 160 nm of wavelength incident on the incoming plane.

3. The attenuated total reflection probe according to claim 1 or 2, wherein the optical material of the prism is one of synthetic quartz, quartz and sapphire.

4. The attenuated total reflection probe according to claim 1 or 2, wherein the optical material of the prism is synthetic quartz, and the supporter is made of synthetic quartz.

5. The attenuated total reflection probe according to claim 1 or 2, wherein the optical material of the prism is sapphire, and the supporter is made of sapphire.

6. The attenuated total reflection probe according to claim 1, wherein the ultraviolet region includes wavelengths between 160 and 180 nm.

7. A spectroscope comprising:
   an attenuated total reflection probe, which comprises: a prism, made of an optical material which has index of refraction higher than water in far ultraviolet region, comprising a contact plane to be in contact with a sample, and an incoming plane and an outgoing plane both not to be in contact with the sample; and a supporter having an opening, connected with optical contact with the prism around the opening, the supporter eventually exposing the contact plane facing the opening; wherein the contact plane, the incoming plane and the outgoing plane of the prism are formed such that light transmitting the incoming plane enters the contact plane at an incident angle larger than critical angle and that the light totally reflected by the contact plane goes out through the outgoing plane;

a light source which radiates ultraviolet light towards the attenuated total reflection probe;

a photodetector which detects light of total reflection received from the attenuated total reflection probe; and an optical element for dispersing ultraviolet light in an optical path from the light source to the photodetector.

* * * * *